(12) United States Patent
Chen

(10) Patent No.: US 10,255,790 B2
(45) Date of Patent: Apr. 9, 2019

(54) USER REMINDING METHOD AND APPARATUS, AND TERMINAL DEVICE

(71) Applicant: Huawei Technologies Co., Ltd., Shenzhen (CN)

(72) Inventor: Wenjuan Chen, Shenzhen (CN)

(73) Assignee: HUAWEI TECHNOLOGIES CO., LTD., Shenzhen (CN)

( * ) Notice: Subject to any disclaimer, the term of this patent is extended or adjusted under 35 U.S.C. 154(b) by 0 days.

(21) Appl. No.: 15/566,359

(22) PCT Filed: Apr. 14, 2015

(86) PCT No.: PCT/CN2015/076564
§ 371 (c)(1),
(2) Date: Oct. 13, 2017

(87) PCT Pub. No.: WO2016/165075
PCT Pub. Date: Oct. 20, 2016

(65) Prior Publication Data
US 2018/0096583 A1    Apr. 5, 2018

(51) Int. Cl.
| | |
|---|---|
| G08B 21/24 | (2006.01) |
| A61M 21/00 | (2006.01) |
| A61B 5/00 | (2006.01) |
| A61B 5/021 | (2006.01) |
| G04G 13/02 | (2006.01) |
| G16H 20/10 | (2018.01) |

(Continued)

(52) U.S. Cl.
CPC ............ *G08B 21/24* (2013.01); *A61B 5/0205* (2013.01); *A61B 5/02108* (2013.01); *A61B 5/02125* (2013.01); *A61B 5/4809* (2013.01); *A61B 5/746* (2013.01); *A61M 21/00* (2013.01); *G04G 13/02* (2013.01); *G16H 20/10* (2018.01); *A61B 5/0402* (2013.01); *A61B 5/4812* (2013.01)

(58) Field of Classification Search
CPC ............................ G08B 21/24; A61B 5/0205
See application file for complete search history.

(56) References Cited

U.S. PATENT DOCUMENTS

| | | |
|---|---|---|
| 2002/0080035 A1 | 6/2002 | Youdenko |
| 2006/0200011 A1 | 9/2006 | Suzuki et al. |

(Continued)

FOREIGN PATENT DOCUMENTS

| | | |
|---|---|---|
| CN | 1388921 A | 1/2003 |
| CN | 1548005 A | 11/2004 |

(Continued)

OTHER PUBLICATIONS

Machine Translation and Abstract of Japanese Publication No. JP2007325613, Dec. 20, 2007, 10 pages.

(Continued)

*Primary Examiner* — Hongmin Fan
(74) *Attorney, Agent, or Firm* — Conley Rose, P.C.

(57) ABSTRACT

A user reminding method and apparatus, and a mobile terminal includes, obtaining, by a terminal device, a physical status of a user and a first blood pressure value of the user when a time difference between a current time and a preset reminding time is less than a first threshold; determining a first safety level based on the physical status and the first blood pressure value; and sending a first reminding signal in a manner corresponding to the first safety level.

20 Claims, 4 Drawing Sheets

(51) Int. Cl.
*A61B 5/0205* (2006.01)
*A61B 5/0402* (2006.01)

(56) References Cited

U.S. PATENT DOCUMENTS

| 2007/0032733 | A1* | 2/2007 | Burton | A61B 5/02405 |
|---|---|---|---|---|
| | | | | 600/509 |
| 2008/0195166 | A1 | 8/2008 | Sun et al. | |
| 2009/0234199 | A1 | 9/2009 | Takahashi et al. | |
| 2010/0228137 | A1 | 9/2010 | Gu | |
| 2016/0081615 | A1 | 3/2016 | Chen | |

FOREIGN PATENT DOCUMENTS

| CN | 101822537 A | 9/2010 |
|---|---|---|
| CN | 102151129 A | 8/2011 |
| CN | 103760761 A | 4/2014 |
| CN | 104095615 A | 10/2014 |
| CN | 104257387 A | 1/2015 |
| JP | 2007325613 A | 12/2007 |
| WO | 2012018029 A1 | 2/2012 |

OTHER PUBLICATIONS

Machine Translation and Abstract of International Publication No. WO2012018029, Feb. 9, 2012, 55 pages.
Foreign Communication From A Counterpart Application, European Application No. 15888780.2, Extended European Search Report dated Feb. 28, 2018, 21 pages.
Machine Translation and Abstract of Chinese Publication No. CN1548005, Nov. 24, 2004, 10 pages.
Machine Translation and Abstract of Chinese Publication No. CN103760761, Apr. 30, 2014, 9 pages.
Machine Translation and Abstract of Chinese Publication No. CN104095615, Oct. 15, 2014, 19 pages.
Foreign Communication From A Counterpart Application, PCT Application No. PCT/CN2015/076564, English Translation of International Search Report dated Jan. 13, 2016, 2 pages.
Foreign Communication From A Counterpart Application, PCT Application No. PCT/CN2015/076564, English Translation of Written Opinion dated Jan. 13, 2016, 6 pages.

* cited by examiner

USER REMINDING METHOD AND APPARATUS, AND TERMINAL DEVICE

CROSS-REFERENCE TO RELATED APPLICATIONS

This application is a national stage application of International Patent Application No. PCT/CN2015/076564, filed on Apr. 14, 2015, which is herein incorporated by reference in its entirety.

TECHNICAL FIELD

Embodiments of the present disclosure relate to the field of electronic products, and in particular, to a user reminding method and apparatus, and a terminal device.

BACKGROUND

Hypertension is one of the most common cardio-cerebral vascular diseases, and an increase in a blood pressure is closely associated with a cardio-cerebral vascular event such as myocardial infarction or cerebral apoplexy, and is an important hidden danger that affects human health.

When a person has a rest at night, a metabolism level is relatively low, and a blood pressure decreases accordingly. Once the person wakes up and gets up to perform an activity, the blood pressure rapidly increases. Duration from 6:00 to 10:00 in the morning is a peak period of a human blood pressure in one day, and a cardio-cerebral vascular event is extremely easily induced in this period because of hypertension.

To smoothly begin one day of life, a user generally sets an alarm in a terminal device, and when the terminal device determines that a current time reaches an alarm time, the alarm rings to prompt the user to get up. The duration from 6:00 to 10:00 in the morning is not only a peak period of a human blood pressure in one day, but also a time period during which most persons need to get up. A sleeping user may feel uncomfortable because of an alarm ringtone that suddenly rings, and may also experience an instantaneous blood pressure increase. Therefore, if a user suffering from hypertension is awakened by an alarm that suddenly rings, a relatively severe event may be induced.

SUMMARY

In view of this, embodiments of the present disclosure provide a user reminding method and apparatus, and a terminal device, so as to avoid a hidden safety danger caused when a sleeping user whose blood pressure increases is suddenly awakened.

According to a first aspect, a user reminding method includes, when a time difference between a current time and a preset reminding time is less than a first threshold, obtaining, by a terminal device, a physical status of a user and a first blood pressure value of the user; determining a first safety level based on the physical status and the first blood pressure value; and sending a first reminding signal in a manner corresponding to the first safety level.

In a first possible implementation manner of the first aspect, the physical status is a sleeping state; and the first reminding signal is an awakening signal.

With reference to the first possible implementation manner of the first aspect, in a second possible implementation manner, after the awakening signal is sent in the manner corresponding to the first safety level, the method further includes, when the terminal device determines that the physical status of the user changes from the sleeping state to an awake state, obtaining a second blood pressure value of the user in the awake state; determining a second safety level based on a difference between the first blood pressure value and the second blood pressure value; and sending a second reminding signal in a manner corresponding to the second safety level.

With reference to the first possible implementation manner of the first aspect, in a third possible implementation manner, after the awakening signal is sent in the manner corresponding to the first safety level, the method further includes, when the terminal device determines that the physical status of the user changes from the sleeping state to an awake state, obtaining a second blood pressure value of the user in the awake state; determining a second safety level based on a difference between the first blood pressure value and the second blood pressure value; determining a third safety level based on the second blood pressure value; and selecting a higher safety level from the second safety level and the third safety level, and sending a third reminding signal in a manner corresponding to the higher safety level.

In a fourth possible implementation manner of the first aspect, the physical status is an awake state; and the first reminding signal is a prompt signal.

With reference to the second possible implementation manner of the first aspect or the third possible implementation manner of the first aspect, in a fifth possible implementation manner, the second reminding signal or the third reminding signal is a prompt signal.

With reference to the first possible implementation manner of the first aspect, the second possible implementation manner of the first aspect, or the third possible implementation manner of the first aspect, in a sixth possible implementation manner, the awakening signal specifically includes normal ringing, soft ringing, or vibration.

With reference to the fourth possible implementation manner of the first aspect or the fifth possible implementation manner of the first aspect, in a seventh possible implementation manner, the prompt signal specifically includes a signal that prompts normal getting-up, a signal that prompts timely medicine taking, a signal that prompts slow getting-up, a signal that prompts still lying, or a signal that prompts help seeking.

According to a second aspect, a user reminding apparatus includes a physical status obtaining unit, a first blood pressure obtaining unit, a first determining unit, and a first reminding unit, where the physical status obtaining unit is configured to, when a time difference between a current time and a preset reminding time is less than a first threshold, obtain a physical status of a user; the first blood pressure obtaining unit is configured to, when the time difference between the current time and the preset reminding time is less than the first threshold, obtain a first blood pressure value of the user; the first determining unit is configured to determine a first safety level based on the physical status obtained by the physical status obtaining unit and the first blood pressure value obtained by the first blood pressure obtaining unit; and the first reminding unit is configured to send a first reminding signal in a manner corresponding to the first safety level determined by the first determining unit.

In a first possible implementation manner of the second aspect, the first reminding unit is specifically configured to, when the physical status of the user obtained by the physical status obtaining unit is a sleeping state, send an awakening signal in the manner corresponding to the first safety level.

With reference to the first possible implementation manner of the second aspect, in a second possible implementation manner, the physical status determining unit is further configured to, after the first reminding unit sends the awakening signal, determine that the physical status of the user changes from the sleeping state to an awake state; the apparatus includes a second blood pressure obtaining unit configured to obtain a second blood pressure value of the user in the awake state; a second determining unit configured to determine a second safety level based on a difference between the first blood pressure value obtained by the first blood pressure obtaining unit and the second blood pressure value obtained by the second blood pressure obtaining unit; and second reminding unit configured to send a second reminding signal in a manner corresponding to the second safety level.

With reference to the first possible implementation manner of the second aspect, in a third possible implementation manner, the apparatus includes the physical status determining unit is further configured to determine that the physical status of the user changes from the sleeping state to an awake state; a second blood pressure obtaining unit configured to obtain a second blood pressure value of the user in the awake state; a second determining unit configured to determine a second safety level based on a difference between the first blood pressure value obtained by the first blood pressure obtaining unit and the second blood pressure value obtained by the second blood pressure obtaining unit; a third determining unit configured to determine a third safety level based on the second blood pressure value obtained by the second blood pressure obtaining unit; and a third reminding unit configured to select a higher safety level from the second safety level and the third safety level, and send a third reminding signal in a manner corresponding to the higher safety level.

In a fourth possible implementation manner of the second aspect, the first reminding unit is specifically configured to, when the physical status of the user obtained by the physical status obtaining unit is an awake state, send a prompt signal in the manner corresponding to the first safety level.

With reference to the second possible implementation manner of the second aspect or the third possible implementation manner of the second aspect, in a fifth possible implementation manner, the second reminding signal or the third reminding signal is a prompt signal.

With reference to the first possible implementation manner of the second aspect, the second possible implementation manner of the second aspect, or the third possible implementation manner of the second aspect, in a sixth possible implementation manner, the awakening signal specifically includes normal alarm ringing, soft ringing, or vibration.

With reference to the fourth possible implementation manner of the second aspect or the fifth possible implementation manner of the second aspect, in a seventh possible implementation manner, the prompt signal specifically includes a signal that prompts normal getting-up, a signal that prompts timely medicine taking, a signal that prompts slow getting-up, a signal that prompts still lying, or a signal that prompts help seeking.

According to a third aspect, a terminal device includes a processor, a storage device, and a communications interface, where the storage device is configured to store computer executable program code; the processor, the storage device, and the communications interface communicate with each other by using a bus; and the processor performs the following operations by reading the program code and data that are stored in the storage device. When a time difference between a current time and a preset reminding time is less than a first threshold, obtaining a physical status of a user and a first blood pressure value of the user; determining a first safety level based on the physical status and the first blood pressure value; and sending a first reminding signal in a manner corresponding to the first safety level.

In a first possible implementation manner of the third aspect, the physical status is a sleeping state; and the first reminding signal is an awakening signal.

With reference to the first possible implementation manner of the third aspect, in a second possible implementation manner, after sending the awakening signal in the manner corresponding to the first safety level, the processor further performs the following operations. Determining that the physical status of the user changes from the sleeping state to an awake state; obtaining a second blood pressure value of the user in the awake state; determining a second safety level based on a difference between the first blood pressure value and the second blood pressure value; and sending a second reminding signal in a manner corresponding to the second safety level.

With reference to the first possible implementation manner of the third aspect, in a third possible implementation manner, after sending the awakening signal in the manner corresponding to the first safety level, the processor further performs the following operations. Determining that the physical status of the user changes from the sleeping state to an awake state; obtaining a second blood pressure value of the user in the awake state; determining a second safety level based on a difference between the first blood pressure value and the second blood pressure value; determining a third safety level based on the second blood pressure value; and selecting a higher safety level from the second safety level and the third safety level, and sending a third reminding signal in a manner corresponding to the higher safety level.

In a fourth possible implementation manner of the third aspect, the physical status is an awake state; and the first reminding signal is a prompt signal.

With reference to the second possible implementation manner of the third aspect or the third possible implementation manner of the third aspect, in a fifth possible implementation manner, the second reminding signal or the third reminding signal is a prompt signal.

With reference to the first possible implementation manner of the third aspect, the second possible implementation manner of the third aspect, or the third possible implementation manner of the third aspect, in a sixth possible implementation manner, the awakening signal includes normal alarm ringing, soft ringing, or vibration.

With reference to the fourth possible implementation manner of the third aspect or the fifth possible implementation manner of the third aspect, in a seventh possible implementation manner, the prompt signal includes a signal that prompts normal getting-up, a signal that prompts timely medicine taking, a signal that prompts slow getting-up, a signal that prompts still lying, or a signal that prompts help seeking.

By means of the foregoing solutions, a safety level of a user is determined according to a physical status and a blood pressure value of the user, and a corresponding reminding manner is customized for the user according to the safety level, thereby avoiding a health risk of the user caused because of a blood pressure change, reducing a blood pressure burden on the user, and then improving safety and comfortableness of ordinary users and hypertension patients who get up in the morning.

DESCRIPTION OF EMBODIMENTS

The following clearly describes the technical solutions in the embodiments of the present disclosure with reference to the accompanying drawings in the embodiments of the present disclosure. The described embodiments are merely some but not all of the embodiments of the present disclosure. All other embodiments obtained by a person of ordinary skill in the art based on the embodiments of the present disclosure without creative efforts shall fall within the protection scope of the present disclosure.

Figure 1:
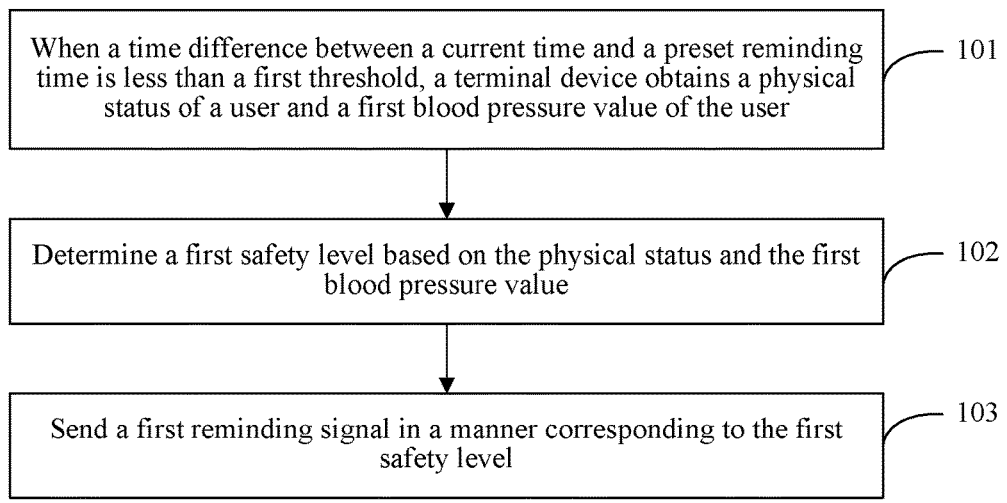
FIG. 1 is a flowchart of a user reminding method according to an embodiment of the present disclosure.

FIG. 1 is a flowchart of a user reminding method according to an embodiment of the present disclosure. As shown in FIG. 1, the method includes the following steps.

Step 101: When a time difference between a current time and a preset reminding time is less than a first threshold, a terminal device obtains a physical status of a user and a first blood pressure value of the user.

In this embodiment of the present disclosure, a time amount of advance, that is, the first threshold is set on the terminal device. When the terminal device determines that the time difference between the current time and the preset reminding time is less than the first threshold, it may be determined that an alarm is to ring, and then the terminal device obtains the physical status and the first blood pressure value of the user.

The first threshold is a time length greater than or equal to a time needed to obtain the physical status and the first blood pressure value of the user, and is, for example, 1 minute, 2 minutes, or another value. The first threshold may be set according to an actual requirement. Certainly, if the first threshold satisfies the foregoing condition, a smaller value of the first threshold indicates that the current time is closer to the preset reminding time, and the physical status and the first blood pressure value that are obtained are greater reference.

In this embodiment of the present disclosure, for example, the physical status of the user may be obtained by using an electrocardiosignal collection apparatus or a pulse wave signal detection apparatus. For example, an electrocardiosignal of the user is detected by using an electrocardiography sensor, and the physical status of the user is determined according to a heart rate and a heart rate variability; a pulse wave period is measured by using an optical sensor, a pressure sensor, an acoustic sensor, a photoelectric sensor, an acceleration sensor, a displacement sensor, or the like, and the physical status is determined according to a change in the pulse wave period. Certainly, as long as apparatuses can obtain the physical status of the user, the apparatuses may be used in this embodiment of the present disclosure, and are not enumerated again herein.

In this embodiment of the present disclosure, the physical status includes, for example, an awake state and a sleeping state. The sleeping state may include, for example, a falling asleep period, a shallow sleep period, a deep sleep period, and a rapid eye movement sleep period, and sleep depths of the falling asleep period, the shallow sleep period, and the deep sleep period are sequentially deepened.

In this embodiment of the present disclosure, for example, the first blood pressure value of the user may be obtained according to results of the electrocardiosignal collection apparatus and the pulse wave signal detection apparatus. For example, an electrocardiosignal of the user is obtained by using the electrocardiosignal collection apparatus, a pulse wave signal of the user is obtained by using the pulse wave signal detection apparatus, a pulse wave transmission time is calculated according to a time interval between a reference point on the electrocardiosignal and a reference point on the pulse wave signal in a same heartbeat period. Because a pulse wave transmission speed is inversely proportional to the pulse wave transmission time, a blood pressure value is calculated according to a relationship between an arterial blood pressure and a pulse wave transmission speed.

For a person of ordinary skill in the art, to calculate a blood pressure value by using an electrocardiosignal and a pulse wave signal is an existing commonly known technology, and how to perform calculation to obtain a blood pressure value may be very easily learned by using an existing reference document. Therefore, details are not described in embodiments of the specification.

Step 102: Determine a first safety level based on the physical status and the first blood pressure value.

A safety level of the user, that is, the first safety level is determined according to the physical status and the first blood pressure value of the user that are obtained in step 101.

A person has different blood pressure values in the awake state and the sleeping state, the person has a relatively low blood pressure value in the sleeping state, and once the person is awake, the blood pressure increases. If the person already has a relatively high blood pressure value in the sleeping state, a risk of inducing a health event due to hypertension exists. Moreover, a deeper sleeping state of the person indicates a lower blood pressure, and if a blood pressure value of the person in a relatively deep sleeping state already reaches a hypertension limit in the awake state, it indicates that a hypertension risk of the person is also higher. Therefore, in this embodiment of the present disclosure, a correspondence is set between different physical statuses and blood pressure values, and corresponding safety levels are set. When a physical status is a rapid eye movement sleep period, physiological characteristics of the person are unstable, and blood pressure fluctuation is relatively large. Therefore, reference value of a blood pressure value of the user in the rapid eye movement sleep period is unobvious, and a safety level is determined with reference to a blood pressure value obtained when the physical status is the awake state.

Blood pressure values corresponding to different grades of the first safety level may be adjusted, for example, according to an actual requirement of the user, or may be preset by a system.

For example, for a correspondence among a first safety level, a physical status, and a blood pressure value in this embodiment of the present disclosure, refer to Table 1 (all blood pressure values in Table 1 are preset by the system, and have a unit of millimeter of mercury (mmHg)).

TABLE 1

| Blood pressure level | First safety level | Physical status | | | | | | | |
|---|---|---|---|---|---|---|---|---|---|
| | | Awake state or rapid eye movement sleep period | | Falling asleep period | | Shallow sleep period | | Deep sleep period | |
| | | Systolic blood pressure | Diastolic blood pressure | Systolic blood pressure | Diastolic blood pressure | Systolic blood pressure | Systolic blood pressure | Systolic blood pressure | Diastolic blood pressure |
| Normal | 0 | <140 | <90 | <135 | <85 | <130 | <80 | <100 | <70 |
| Mild hypertension | 1 | ≥140, <160 | ≥90, <100 | ≥135, <155 | ≥85, <95 | ≥130, <150 | ≥80, <90 | ≥120, <140 | ≥70, <80 |
| Moderate hypertension | 2 | ≥160, <180 | ≥100, <110 | ≥155, <175 | ≥95, <105 | ≥150, <170 | ≥90, <100 | ≥140, <160 | ≥80, <90 |
| Severe hypertension | 3 | ≥180 | ≥110 | ≥175 | ≥105 | ≥170 | ≥100 | ≥160 | ≥90 |

For ease of description, when each of a blood pressure value, a diastolic blood pressure, and a systolic blood pressure is mentioned below, a unit of mmHg is omitted.

For example, referring to Table 1, when the obtained physical status of the user is the shallow sleep period in the sleeping state, and a systolic blood pressure is 135 and a diastolic blood pressure is 86 in the obtained first blood pressure value of the user, the foregoing table is searched based on the physical status and the first blood pressure value, to determine that the first safety level of the user is 1, that is, the user has mild hypertension.

Further, optionally, when a systolic blood pressure and a diastolic blood pressure belong to different blood pressure levels respectively, a higher one of blood pressure levels of the systolic blood pressure and the diastolic blood pressure is used as a standard for determining the first safety level.

For example, when the obtained physical status of the user is the shallow sleep period in the sleeping state, a systolic blood pressure is 135, and a diastolic blood pressure is 95, because the diastolic blood pressure corresponds to a higher blood pressure level, it is determined, according to that the diastolic blood pressure is 95, that the first safety level of the user is 2, that is, the user has moderate hypertension.

Step 103: Send a first reminding signal in a manner corresponding to the first safety level.

Users at different grades in the first safety level have different external environment requirements. For a user who is already awake, a blood pressure status of the user and a behavior of the user after the user gets up need to be learned. For a user who is sleeping, if the user has no hypertension history, even if the user is suddenly awakened, a blood pressure of the user does not increase. However, for a user who has a hypertension history or is in a hypertension state, if the user is awakened by an alarm ringtone that suddenly rings, a temporary disorder of nerves and endocrine is caused, and a blood pressure is further increased. For example, if a sleeping user having moderate hypertension suddenly hears ringing of an alarm ringtone and is awakened, a blood pressure value may increase, and reach a range of severe hypertension. Moreover, regardless of whether a hypertension emergency state or a hypertension crisis occurs in a hypertension patient, and regardless of whether an uncomfortable symptom occurs in the hypertension patient, as long as a systolic blood pressure exceeds 180 mmHg or a diastolic blood pressure exceeds 110 mmHg, antihypertensive therapy should be performed on the hypertension patient in time; otherwise, the life of the hypertension patient is probably endangered.

Therefore, in this embodiment of the present disclosure, the first reminding signal is sent in the manner corresponding to the first safety level. In this way, users at different grades in the first safety level receive different reminding signals sent by the terminal device, thereby improving comfortableness and safety of getting up in the morning.

In this embodiment of the present disclosure, a safety level of a user is determined according to a physical status and a blood pressure value of the user, and a corresponding reminding manner is customized for the user according to the safety level, thereby avoiding a health risk of the user caused because of a blood pressure change, reducing a blood pressure burden on the user, and then improving safety and comfortableness of ordinary users and hypertension patients who get up in the morning.

Figure 2:
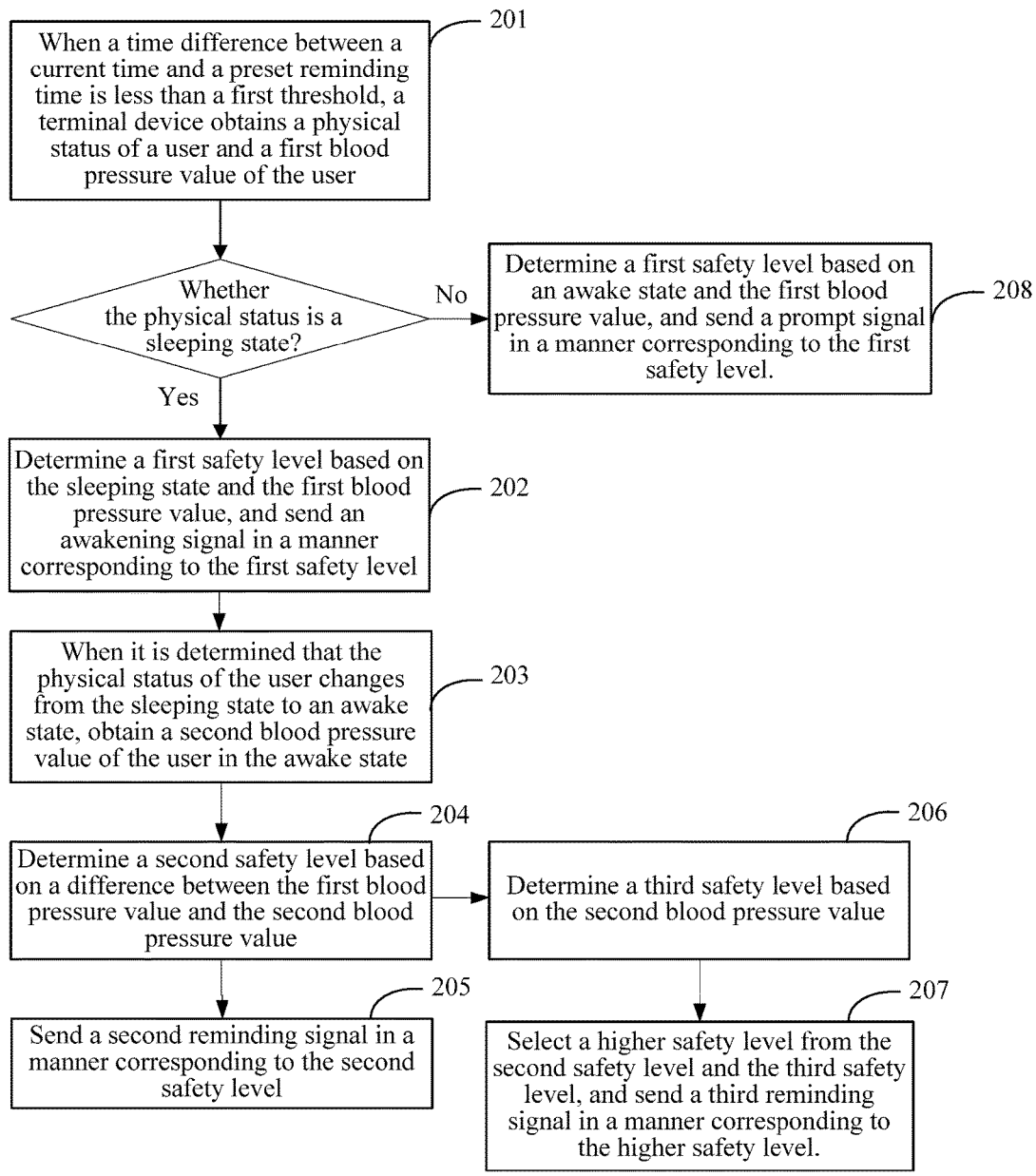
FIG. 2 is a flowchart of another user reminding method according to an embodiment of the present disclosure.

FIG. 2 is a schematic diagram of another user reminding method according to an embodiment of the present disclosure. On the basis of the user reminding method shown in FIG. 1, as shown in FIG. 2, the method includes the following steps.

Step 201: When a time difference between a current time and a preset reminding time is less than a first threshold, a terminal device obtains a physical status of a user and a first blood pressure value of the user; and when the physical status is a sleeping state, perform step 202; or when the physical status is an awake state, perform step 208.

Step 202: Determine a first safety level based on the sleeping state and the first blood pressure value, and send an awakening signal in a manner corresponding to the first safety level.

It should be noted that, the awakening signal includes but is not limited to normal alarm ringing, soft ringing, or vibration.

The awakening signal may be preset, or may be selected by the user. For example, a health risk caused by hypertension to a user having chronic hypertension is larger than that caused by hypertension to a user having no hypertension history, and therefore, a user may adjust a systolic blood pressure value and a diastolic blood pressure value in Table 1 of the first safety level, and select a corresponding awakening signal.

In this embodiment of the present disclosure, the awakening signal may be preset, for example, in the following manners.

The first safety level is 0, and it indicates that a measured user has a normal blood pressure, and no hidden safety danger is caused because of an abnormal blood pressure. Therefore, the awakening signal is a normal alarm ringtone, and the user is awakened from sleep by using the normal alarm ringtone.

The first safety level is 1, and it indicates that a measured user has mild hypertension, and if the user is suddenly awakened by an alarm, the user feels uncomfortable, and has a relatively low risk. Therefore, the awakening signal is soft ringing, and the user is awakened from sleep by using soft and soothing music, thereby improving comfortableness of the awakened user.

The first safety level is 2, and it indicates that a measured user has moderate hypertension, and a blood pressure of the user may continue to increase because an alarm suddenly rings; not only the user feels uncomfortable, but also a health risk is induced. Therefore, the awakening signal is vibration, and the user is awakened from sleep by means of vibration, that is, an alarm ringtone is disabled, and a prompt of an alarm is perceived by using body or skin touch, so as to awaken the user, thereby avoiding a blood pressure increase caused because of scare, and improving safety and comfortableness of the user.

The first safety level is 3, and it indicates that a measured user has severe hypertension, and if the user is suddenly awakened by an alarm ringtone, there is a great risk of instantaneously increasing a blood pressure, and then endangering the life. Therefore, the terminal device sends no awakening signal, that is, an alarm is disabled. For example, the terminal device may send an instruction to an intelligent residential system, to adjust light in a bedroom, so as to naturally awaken the user, or notify a family of the user, and the user may be awakened from sleep with the help of the family.

Step 203: When the terminal device determines that the physical status of the user changes from the sleeping state to an awake state, obtain a second blood pressure value of the user in the awake state.

In step 202, after the terminal device sends a reminding signal, the user may be awakened. In this case, the terminal device may detect that the physical status of the user changes from the sleeping state to the awake state.

The second blood pressure value of the user in the awake state is obtained based on a manner the same as that of obtaining the first blood pressure value in step 101 in Embodiment 1, and details are not described herein again.

Step 204: Determine a second safety level based on a difference between the first blood pressure value and the second blood pressure value.

A change between blood pressure values of a user having no hypertension history in the sleeping state and the awake state is an approximate constant such as 10 to 20 mmHg. If a change between blood pressure values of a user in the sleeping state and the awake state exceeds this approximate constant, it indicates that a blood pressure of the user fluctuates relatively largely, and a health risk is induced because of hypertension.

The first blood pressure value is compared with the second blood pressure value, a blood pressure difference between systolic blood pressures of the first blood pressure value and the second blood pressure value and a blood pressure difference between diastolic blood pressures of the first blood pressure value and the second blood pressure value are separately determined, and the second safety level is determined according to a larger one of the blood pressure difference between the systolic blood pressures and the blood pressure difference between the diastolic blood pressures.

Blood pressure differences at safety levels may be adjusted, for example, according to an actual requirement of the user, or may be preset by a system.

For example, for a correspondence between a second safety level and a blood pressure difference in this embodiment of the present disclosure, refer to Table 2 (all blood pressure differences in Table 2 are preset by the system).

TABLE 2

| Second safety level | Blood pressure difference mmHg |
|---|---|
| 0 | <20 |
| 1 | ≥20, <40 |
| 2 | ≥40, <60 |
| 3 | ≥60 |

For example, a physical status of a user is a shallow sleep period in a sleeping state, a systolic blood pressure of the obtained first blood pressure value is 135, and a diastolic blood pressure of the obtained first blood pressure value is 86. When it is determined that the physical status of the user changes from the sleeping state to an awake state, a systolic blood pressure of the obtained second blood pressure value is 145, and a diastolic blood pressure of the obtained second blood pressure value is 107. Therefore, when the physical status of the user changes from the sleeping state to the awake state, a difference between the systolic blood pressures is 10, and a difference between the diastolic blood pressures is 21. In this case, a larger value 21 of the difference between the systolic blood pressures and the difference between the diastolic blood pressures is selected, and Table 2 is searched to determine that the second safety level of the blood pressure of the awakened user is 1.

Step 205: Send a second reminding signal in a manner corresponding to the second safety level.

According to step 204, after the second safety level of the user is determined, the second reminding signal is sent in the manner corresponding to the second safety level.

A higher second safety level indicates a larger blood pressure change, and a higher health risk caused by the blood pressure change. Therefore, when the second reminding signal is sent in a manner corresponding to a different second safety level, it can be ensured that the user does not suddenly get up without being informed, which aggravates a blood pressure burden, and causes a health risk.

Further, in this embodiment of the present disclosure, the second reminding signal is a prompt signal.

It should be noted that, the prompt signal involved in this embodiment of the present disclosure includes but is not limited to a signal that prompts normal getting-up, a signal that prompts timely medicine taking, a signal that prompts slow getting-up, a signal that prompts still lying, or a signal that prompts help seeking.

The second reminding signal sent in the manner corresponding to the second safety level in Table 2 may be, for example, preset on the following manner.

The second safety level is 0, and it indicates that a blood pressure of a measured user fluctuates normally, and no hidden safety danger is caused because of an abnormal blood pressure. Therefore, the prompt signal is, for example, a simple speech prompt such as "healthy" or "not bad today", to remind the user that the user may normally get up, and certainly, there may be no reminding.

The second safety level is 1, and it indicates that a blood pressure of a measured user fluctuates slightly highly, there is a potential risk of hypertension, and attention should be paid to a blood pressure change. Therefore, the prompt signal is, for example, a message pushed to a mobile phone or a wearable device in a form of speech or text such as "blood pressure is slightly high, and please pay attention", or "take medicine in time", to remind the user to get up normally and take medicine in time, thereby improving a health index of the user.

Further, when it is determined that the second safety level is 1, while sending the prompt signal, the terminal device or a wearable device may further directly set a medicine taking time, that is, set a second threshold, thereby reminding the user to take medicine at a time after the second threshold starting from a current time, to control a blood pressure, so as to prevent the user from delaying an illness status due to forgetting to take medicine.

The second safety level is 2, and it indicates that a blood pressure of a measured user fluctuates relatively largely, and direct getting-up may cause the body to feel uncomfortable. Therefore, the prompt signal is, for example, a message pushed to a mobile phone or a wearable device in a form of speech or text such as "blood pressure is relatively high, and please get up slowly and take medicine on time", "blood pressure is relatively high, and please lie still and take medicine on time", or "please not act violently and take medicine on time", to remind the user to get up slowly, or to lie still in a bed for a period of time and then get up slowly, or not to act violently after getting up, and take medicine on time, or see a doctor at once if necessary, thereby improving vigilance of the user, and paying attention to a blood pressure change in real time.

Further, optionally, when it is determined that the second safety level is 2, in a period when a user lies still according to reminding of the terminal device, the second blood pressure value of the user at the time of waking up is detected continuously at a fixed interval, and when it is determined that a blood pressure difference between the second blood pressure value and the first blood pressure value of the user decreases and falls within a range corresponding to the second safety level being 1, the user is reminded in a reminding manner of the second safety level being 1, to get up and take medicine.

The second safety level is 3, and it indicates that blood pressure fluctuation of a measured user exceeds a limit, and direct getting-up has a high health risk. Therefore, the prompt signal is, for example, reminding the user of "blood pressure is very high, and please lie still" by using speech, to remind the user not to get up, and send help seeking information to a family or a doctor.

Further, optionally, when it is determined that the second safety level is 3, in a period when a user lies still according to reminding of the terminal device, the second blood pressure value of the user at the time of waking up is monitored continuously at a fixed interval, and when it is determined that a blood pressure difference between the second blood pressure value and the first blood pressure value of the user decreases to another second safety level, the user is reminded in a prompt manner of the another second safety level.

Further, optionally, in this embodiment of the present disclosure, after step 201 to step 204, step 205 is not performed, but instead, step 206 and step 207 are directly performed.

Step 206: Determine a third safety level based on the second blood pressure value of the user in the awake state. The third safety level may be determined with reference to, for example, a medical standard blood pressure value. Refer to Table 3.

TABLE 3

| Blood pressure level | Third safety level | Blood pressure range mmHg | |
|---|---|---|---|
| Normal | 0 | systolic blood pressure < 140 | diastolic blood pressure < 90 |
| Mild hypertension | 1 | 140 ≤ systolic blood pressure < 159 | 90 ≤ diastolic blood pressure < 99 |
| Moderate hypertension | 2 | 160 ≤ systolic blood pressure < 179 | 100 ≤ diastolic blood pressure < 109 |
| Severe hypertension | 3 | systolic blood pressure ≥ 180 | diastolic blood pressure ≥ 110 |

Step 207: Select a higher safety level from the second safety level and the third safety level, and send a third reminding signal in a manner corresponding to the higher safety level. After step 207, the embodiment provided in the method ends.

For example, when the second safety level corresponding to the blood pressure difference between the second blood pressure value and the first blood pressure value of the user is 2, and the third safety level corresponding to the second blood pressure value of the user is 1, the third reminding signal is sent in a manner corresponding to the higher second safety level being 2.

It should be noted that, in this embodiment of the present disclosure, the third reminding signal may be the same as the second reminding signal, that is, the third reminding signal is also a prompt signal.

Step 208: Determine a first safety level based on the awake state and the first blood pressure value, and send a prompt signal in a manner corresponding to the first safety level.

The prompt signal may be the same as the second reminding signal or the third reminding signal, and includes but is not limited to a signal that prompts normal getting-up, a signal that prompts timely medicine taking, a signal that prompts slow getting-up, a signal that prompts still lying, or a signal that prompts help seeking.

According to this embodiment of the present disclosure, a safety level of a user is determined according to a physical status and a blood pressure value of the user, a corresponding reminding manner is customized for the user according to the safety level, and a reminding manner after awaking is further provided for a case in which the physical status is a sleeping state, so as to ensure safety of the user when the user gets up in the morning, and reduce a health risk.

An embodiment of the present disclosure further provides a user reminding apparatus for implementing steps and methods in the foregoing method embodiments.

Figure 3:
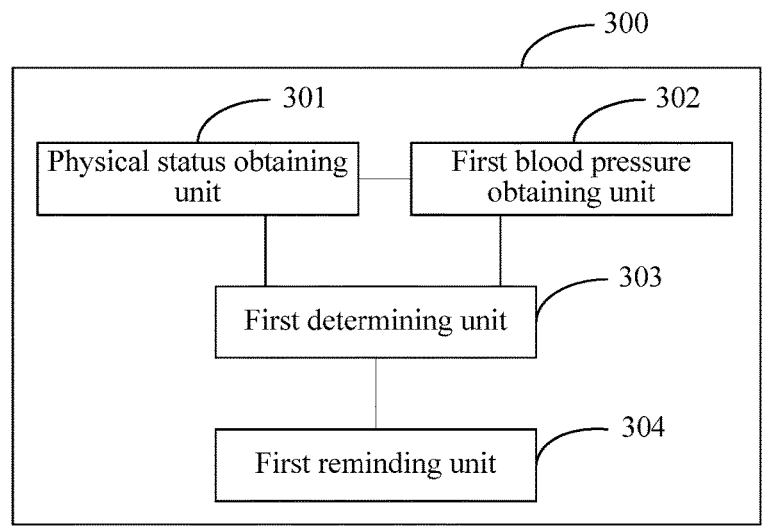
FIG. 3 is a schematic diagram of a user reminding apparatus according to an embodiment of the present disclosure.

FIG. 3 is a schematic diagram of a user reminding apparatus according to an embodiment of the present disclosure. As shown in FIG. 3, the apparatus 300 includes a physical status obtaining unit 301, a first blood pressure obtaining unit 302, a first determining unit 303, and a first reminding unit 304.

The physical status obtaining unit 301 is configured to, when a time difference between a current time and a preset reminding time is less than a first threshold, obtain a physical status of a user.

The first blood pressure obtaining unit 302 is configured to, when the time difference between the current time and the preset reminding time is less than the first threshold, obtain a first blood pressure value of the user.

The first determining unit 303 is configured to determine a first safety level based on the physical status obtained by the physical status obtaining unit and the first blood pressure value obtained by the first blood pressure obtaining unit.

The first reminding unit 304 is configured to send a first reminding signal in a manner corresponding to the first safety level determined by the first determining unit.

In this embodiment of the present disclosure, a safety level of a user is determined according to a physical status and a blood pressure value of the user, and a corresponding reminding manner is customized for the user according to the safety level, thereby avoiding a health risk of the user caused because of a blood pressure change, reducing a blood pressure burden on the user, and then improving safety and comfortableness of ordinary users and hypertension patients who get up in the morning.

The user reminding apparatus provided in this embodiment of the present disclosure is configured to implement the methods shown in the embodiments shown in FIG. 1 and FIG. 2. For details of an operating principle and an operating process of the user reminding apparatus and a technical effect generated by the user reminding apparatus, refer to the embodiments shown in FIG. 1 and FIG. 2, and details are not described herein again.

Figure 4:
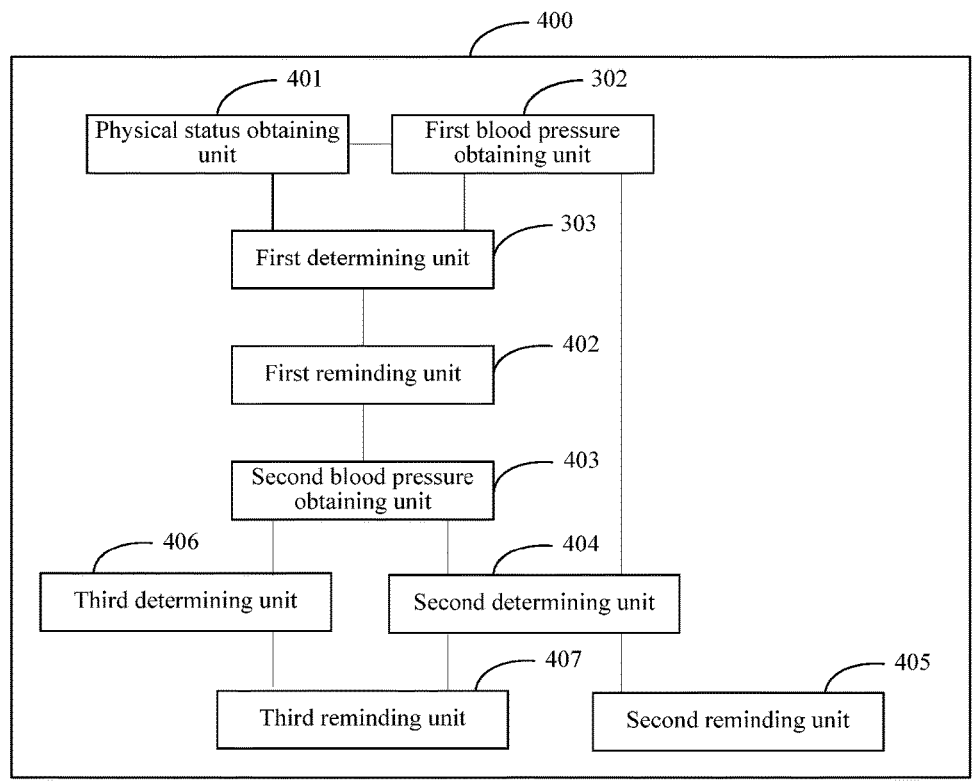
FIG. 4 is a schematic diagram of another user reminding apparatus according to an embodiment of the present disclosure.

FIG. 4 is a schematic diagram of another user reminding apparatus according to an embodiment of the present disclosure. On the basis of Embodiment 3 shown in FIG. 3, as shown in FIG. 4, the apparatus 400 includes a physical status obtaining unit 401 configured to, when a time difference between a current time and a preset reminding time is less than a first threshold, obtain that a physical status of a user is a sleeping state; a first reminding unit 402 configured to send an awakening signal in a manner corresponding to the first safety level determined by the first determining unit 303, where the physical status determining unit 401 is further configured to, after the first reminding unit 402 sends the awakening signal, determine that the physical status of the user changes from the sleeping state to an awake state; a second blood pressure obtaining unit 403 configured to obtain a second blood pressure value of the user in the awake state; a second determining unit 404 configured to determine a second safety level based on a difference between the first blood pressure value and the second blood pressure value; and a second reminding unit 405 configured to send a second reminding signal in a manner corresponding to the second safety level determined by the second determining unit 404.

It should be noted that, the second reminding signal may be, for example, a prompt signal, and the prompt signal includes but is not limited to a signal that prompts normal getting-up, a signal that prompts timely medicine taking, a signal that prompts slow getting-up, a signal that prompts still lying, or a signal that prompts help seeking.

Further, optionally, in a case in which the foregoing units 401 to 404 in this embodiment of the present disclosure are included, the second reminding unit 405 may not be included, but instead, a third determining unit 406 and a third reminding unit 407 are included.

The third determining unit 406 is configured to determine a third safety level based on the second blood pressure value obtained by the second blood pressure obtaining unit 403.

The third reminding unit 407 is configured to select a higher safety level from the second safety level and the third safety level, and send a third reminding signal in a manner corresponding to the higher safety level.

It should be noted that, the third reminding signal may be the same as the second reminding signal, and is, for example, a prompt signal.

In this embodiment of the present disclosure, it is determined, according to a blood pressure difference between a first blood pressure value of a user in a sleeping state and a second blood pressure value of the user whose status changes from the sleeping state to an awake state, whether the user has a health risk caused by hypertension, and the user is reminded, by using different reminders, of sitting-up manners that the user may use, thereby further ensuring safety of the user getting up in the morning, and reducing a health risk.

The user reminding apparatus provided in this embodiment of the present disclosure is configured to implement the methods shown in the embodiments shown in FIG. 1 and FIG. 2. For details of an operating principle and an operating process of the user reminding apparatus and a technical effect generated by the user reminding apparatus, refer to the embodiments shown in FIG. 1 and FIG. 2, and details are not described herein again.

Figure 5:
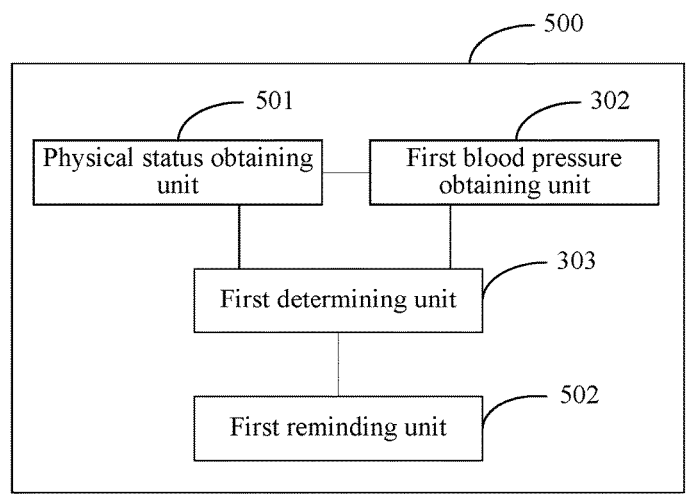
FIG. 5 is a schematic diagram of another user reminding apparatus according to an embodiment of the present disclosure.

FIG. 5 shows another user reminding apparatus according to an embodiment of the present disclosure. On the basis of the embodiment shown in FIG. 3, as shown in FIG. 5, the apparatus includes a physical status obtaining unit 501 configured to, when a time difference between a current time and a preset reminding time is less than a first threshold, obtain that a physical status of a user is an awake state; and a first reminding unit 502 configured to, when the physical status of the user obtained by the physical status obtaining unit is an awake state, send a prompt signal in the manner corresponding to the first safety level.

In this embodiment of the present disclosure, a first blood pressure value is obtained when a physical status of a user is an awake state, a first safety level is determined according to the awake state and the first blood pressure value, and a signal reminding the user of a sitting-up manner is sent in a manner corresponding to the first safety level, thereby ensuring safety of the user getting up in the morning, and reducing a health risk.

The user reminding apparatus provided in this embodiment of the present disclosure is configured to implement the methods shown in the embodiments shown in FIG. 1 and FIG. 2. For details of an operating principle and an operating process of the user reminding apparatus and a technical effect generated by the user reminding apparatus, refer to the embodiments shown in FIG. 1 and FIG. 2, and details are not described herein again.

Figure 6:
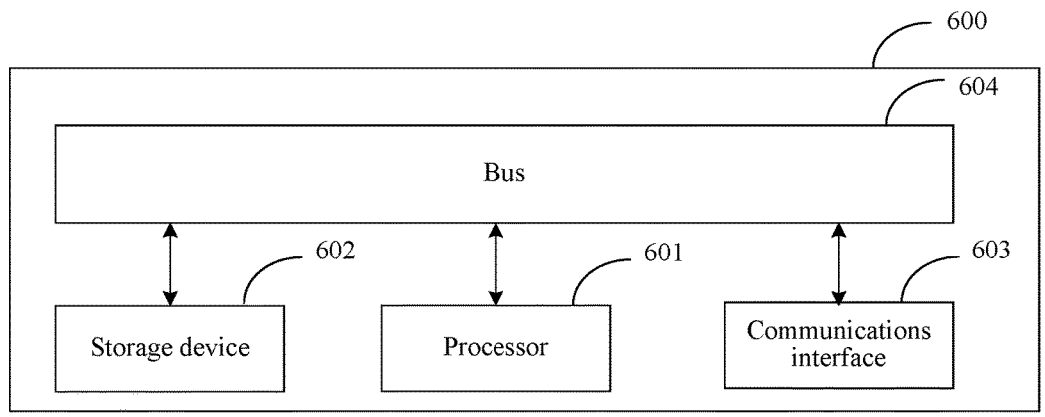
FIG. 6 is a schematic diagram of a terminal device according to an embodiment of the present disclosure.

FIG. 6 is a schematic diagram of a terminal device according to an embodiment of the present disclosure.

The terminal device 600 in this embodiment of the present disclosure includes a processor 601 coupled to one or more storage devices, a storage device 602, a communications interface 603, and a bus 604.

The processor 601 is a control center of the terminal device 600 and provides sequencing and processing facilities to execute an instruction, perform an interrupt operation, and provide a timing function and many other functions. Optionally, the processor 601 includes one or more central processing units (CPU). Optionally, the terminal device 600 includes more than one processor. The processor 601 may be a single-core (single-CPU) processor or a multi-core (multi-CPU) processor. The term "processor" used in this specification refers to one or more devices, circuits, and/or processing kernels configured to process data such as a computer program instruction.

The storage device 602 may include a storage medium and a memory unit. The storage medium may be read-only such as a read-only memory (ROM), or be readable/writable such as a hard disk or flash memory. The memory unit may be a random access memory (RAM). The memory unit may be physically integrated together with the processor 601 or be integrated into the processor 601 or be constructed in one or more independent units.

The processor 601 may execute program code stored in the storage device 602. Optionally, the program code stored in the storage medium of the storage device 602 may be replicated into the memory unit, so as to be executed by the processor. The processor may execute at least one kernel (for example, a kernel in an operating system sold with a trademark such as LINUX®, UNIX®, WINDOWS®, ANDROID®, or IOS®), and it is well known that the kernel is configured to control operations of the terminal device 600 by controlling execution of other programs or processes, controlling communication with a peripheral, and controlling use of resources of a computing device.

The terminal device 600 further includes the communications interface 603 configured to communicate with another device or system directly or by using an external network.

The foregoing elements of the terminal device 600 may be coupled to each other by using any one of or any combination of the bus 604 such as a data bus, an address bus, a control bus, an extended bus or a local bus.

Optionally, the terminal device 600 further includes an output device and an input device (not shown). The output device is coupled to the processor 601, and can display information in one or more manners. An example of the output device is a visual display device, for example, a liquid crystal display (LCD), a light emitting diode (LED) display, a cathode-ray tube (CRT), or a projector. The input device is also coupled to the processor 601, and can receive a user input of the terminal device 600 in one or more manners. An example of the input device includes a mouse, a keyboard, a touchscreen device, a sensing device, or the like.

The processor 601 reads the program code and data that are stored in the storage device 602, where the program code includes an instruction, and when executing the instruction, the processor performs the following operations. When a time difference between a current time and a preset reminding time is less than a first threshold, obtaining a physical status of a user and a first blood pressure value of the user; determining a first safety level based on the physical status and the first blood pressure value; and sending a first reminding signal in a manner corresponding to the first safety level.

It should be noted that, when the terminal device 600 of this embodiment of the present disclosure is a wearable device, the wearable device includes an electrocardiosignal collection apparatus and a pulse wave signal collection apparatus, and the processor 601 controls the electrocardiosignal collection apparatus and the pulse wave signal collection apparatus to obtain an electrocardiosignal and a pulse wave signal, obtains the physical status according to the electrocardiosignal and/or the pulse wave signal, and obtains the first blood pressure value of the user according to the electrocardiosignal and the pulse wave signal. The processor 601 determines the first safety level based on the physical status and the first blood pressure value that are obtained, and sends the first reminding signal in the manner corresponding to the first safety level.

Optionally, when the terminal device 600 of this embodiment of the present disclosure is a general-purpose computing device or an application-specific computing device such as a desktop computer, a notebook computer, a network server, a personal digital assistant (PDA), a mobile phone, a tablet computer, a wireless terminal device, a telecommunications device, an embedded system or any other device that has a structure similar to that shown in FIG. 6, the processor 601 of the terminal device 600 needs to obtain a physical status and a blood pressure value of a user by using a wearable device including an electrocardiosignal collection apparatus and a pulse wave signal collection apparatus. That is, the processor 601 controls the electrocardiosignal collection apparatus and pulse wave signal collection apparatus in the wearable device to perform the operation of obtaining the physical status and the blood pressure value, and receives obtained data returned by the wearable device. The processor 601 determines the first safety level based on the physical status and the first blood pressure value that are obtained, and sends the first reminding signal in the manner corresponding to the first safety level.

Further, when the physical status is an awake state, the processor 601 sends a prompt signal in the manner corresponding to the first safety level.

It should be noted that, in this embodiment of the present disclosure, the prompt signal includes but is not limited to a signal that prompts normal getting-up, a signal that prompts timely medicine taking, a signal that prompts slow getting-up, a signal that prompts still lying, or a signal that prompts help seeking.

Further, when the physical status is a sleeping state, the processor 601 sends an awakening signal in the manner corresponding to the first safety level.

It should be noted that, in this embodiment of the present disclosure, the awakening signal includes but is not limited to normal alarm ringing, soft ringing, or vibration.

Further, after sending the awakening signal in the manner corresponding to the first safety level, the processor 601 further performs the following operations. Determining that the physical status of the user changes from the sleeping state to an awake state; obtaining a second blood pressure value of the user in the awake state; determining a second safety level based on a difference between the first blood pressure value and the second blood pressure value; and sending a second reminding signal in a manner corresponding to the second safety level.

Further, after sending the awakening signal in the manner corresponding to the first safety level, the processor 601 further performs the following operations. Determining that the physical status of the user changes from the sleeping state to an awake state; obtaining a second blood pressure value of the user in the awake state; determining a second safety level based on a difference between the first blood pressure value and the second blood pressure value; determining a third safety level based on the second blood pressure value; and selecting a higher safety level from the second safety level and the third safety level, and sending a third reminding signal in a manner corresponding to the higher safety level.

It should be noted that, in this embodiment of the present disclosure, the second reminding signal or the third reminding signal is a prompt signal.

In this embodiment of the present disclosure, a safety level of a user is determined according to a physical status and a blood pressure value of the user, and a corresponding reminding manner is customized for the user according to the safety level, thereby avoiding a health risk of the user caused because of a blood pressure change, reducing a blood pressure burden on the user, and then improving safety and comfortableness of ordinary users and hypertension patients who get up in the morning.

The terminal device provided in this embodiment of the present disclosure is configured to implement the methods shown in the embodiments shown in FIG. 1 and FIG. 2. For details of an operating principle and an operating process of the terminal device and a technical effect generated by the terminal device, refer to the embodiments shown in FIG. 1 and FIG. 2, and details are not described herein again.

With descriptions of the foregoing embodiments, a person skilled in the art may clearly understand that the present disclosure may be implemented by hardware, firmware or a combination thereof. When the present disclosure is implemented by software, the foregoing functions may be stored in a computer-readable medium or transmitted as one or more instructions or code in the computer-readable medium. The computer-readable medium includes a computer storage medium and a communications medium, where the communications medium includes any medium that enables a computer program to be transmitted from one place to another. The storage medium may be any available medium accessible to a computer. The following provides an example but does not impose a limitation. The computer-readable medium may include a RAM, a ROM, an electrically erasable programmable read only memory (EEPROM), a Compact Disc read-only-memory (CD-ROM), or another optical disc storage or a disk storage medium, or another magnetic storage device, or any other medium that can carry or store expected program code in a form of an instruction or a data structure and can be accessed by a computer. In addition, any connection may be appropriately defined as a computer-readable medium. For example, if software is transmitted from a website, a server or another remote source by using a coaxial cable, an optical fiber/cable, a twisted pair, a digital subscriber line (DSL) or wireless technologies such as infrared ray, radio and microwave are included in fixation of a medium to which they belong. For example, a disk and disc used by the present disclosure includes a compact disc (CD), a laser disc, an optical disc, a digital versatile disc (DVD), a floppy disk and a Blu-ray disc, where the disk generally copies data by a magnetic means, and the disc copies data optically by a laser means. The foregoing combination should also be included in the protection scope of the computer-readable medium.

In summary, what is described above is merely exemplary embodiments of the technical solutions of the present disclosure, but is not intended to limit the protection scope of the present disclosure. Any modification, equivalent replacement, or improvement made without departing from the spirit and principle of the present disclosure shall fall within the protection scope of the present disclosure.

What is claimed is:

1. A user reminding method, comprising:
obtaining, by a terminal device, a physical status of a user and a first blood pressure value of the user when a time difference between a current time and a preset reminding time is less than a first threshold time;
determining, by the terminal device, a first safety level based on the physical status of the user and the first blood pressure value of the user; and
sending, by the terminal device, a first reminding signal in a manner corresponding to the first safety level.

2. The method of claim 1, wherein the physical status is a sleeping state, and the first reminding signal being an awakening signal.

3. The method of claim 2, further comprising:
obtaining a second blood pressure value of the user in an awake state when the physical status of the user changes from the sleeping state to the awake state;
determining a second safety level based on a difference between the first blood pressure value and the second blood pressure value; and
sending a second reminding signal in a manner corresponding to the second safety level.

4. The method of claim 2, further comprising:
obtaining a second blood pressure value of the user in an awake state when the physical status of the user changes from the sleeping state to the awake state;
determining a second safety level based on a difference between the first blood pressure value and the second blood pressure value;
determining a third safety level based on the second blood pressure value;
selecting a higher safety level from the second safety level and the third safety level; and
sending a third reminding signal in a manner corresponding to the higher safety level.

5. The method of claim 1, wherein the physical status is an awake state, and the first reminding signal being a prompt signal.

6. The method of claim 3, wherein either the second reminding signal or a third reminding signal is a prompt signal.

7. The method of claim 6, wherein the awakening signal comprises normal ringing, soft ringing, or vibration, and the prompt signal comprising either a first signal to indicate to the user to get-up normally, a second signal to indicate a time to the user to take medicine, a third signal to indicate to the user to get-up slowly, a fourth signal to indicate to the user to lay still, or a fourth signal to indicate to the to can seek help.

8. A terminal device, comprising:
a memory storing instructions; and
a processor coupled to the memory, the instructions causing the processor to be configured to:
obtain a physical status of a user and a first blood pressure value of the user when a time difference between a current time and a preset reminding time is less than a first threshold;
determine a first safety level based on the physical status of the user and the first blood pressure value of the user; and
send a first reminding signal in a manner corresponding to the first safety level.

9. The terminal device of claim 8, wherein the physical status is a sleeping state, and the first reminding signal being an awakening signal.

10. The terminal device of claim 9, wherein the instructions further cause the processor to be configured to:
determine that the physical status of the user changes from the sleeping state to an awake state;
obtain a second blood pressure value of the user in the awake state;
determine a second safety level based on a difference between the first blood pressure value and the second blood pressure value; and
send a second reminding signal in a manner corresponding to the second safety level.

11. The terminal device of claim 9, wherein the instructions further cause the processor to be configured to:
determine that the physical status of the user changes from the sleeping state to an awake state;
obtain a second blood pressure value of the user in the awake state;
determine a second safety level based on a difference between the first blood pressure value and the second blood pressure value;
determine a third safety level based on the second blood pressure value;

select a higher safety level from the second safety level and the third safety level; and send a third reminding signal in a manner corresponding to the higher safety level.

12. The terminal device of claim 8, wherein the physical status is an awake state, and the first reminding signal being a prompt signal.

13. The terminal device of claim 10, wherein either the second reminding signal or a third reminding signal is a prompt signal.

14. The terminal device of claim 13, wherein the awakening signal comprises either normal alarm ringing, soft ringing, or vibration, and the prompt signal comprising either a first signal to indicate to the user to get-up normally, a second signal to indicate a time to the user to take medicine, a third signal to indicate to the user to get-up slowly, a fourth signal to indicate to the user to lay still, or a fourth signal to indicate to the user to seek help.

15. A non-transitory computer readable medium including at least one computer program code stored therein for user reminding on a device associated with a computing device wherein when executed on a processor, the non-transitory computer readable medium causing the processor to be configured to:

obtain a physical status of a user and a first blood pressure value of the user when a time difference between a current time and a preset reminding time is less than a first threshold;

determine a first safety level based on the physical status of the user and the first blood pressure value of the user; and send a first reminding signal in a manner corresponding to the first safety level.

16. The non-transitory computer readable medium of claim 15, wherein the physical status is a sleeping state, and the first reminding signal being an awakening signal.

17. The non-transitory computer readable medium of claim 16, wherein the non-transitory computer readable medium further causes the processor to be configured to:

determine that the physical status of the user changes from the sleeping state to an awake state;

obtain a second blood pressure value of the user in the awake state;

determine a second safety level based on a difference between the first blood pressure value and the second blood pressure value; and send a second reminding signal in a manner corresponding to the second safety level.

18. The non-transitory computer readable medium of claim 16, wherein the non-transitory computer readable medium further causes the processor to be configured to:

determine that the physical status of the user changes from the sleeping state to an awake state;

obtain a second blood pressure value of the user in the awake state;

determine a second safety level based on a difference between the first blood pressure value and the second blood pressure value;

determine a third safety level based on the second blood pressure value;

select a higher safety level from the second safety level and the third safety level; and send a third reminding signal in a manner corresponding to the higher safety level.

19. The non-transitory computer readable medium of claim 15, wherein the physical status is an awake state, and the first reminding signal being a prompt signal.

20. The non-transitory computer readable medium of claim 17, wherein either the second reminding signal or a third reminding signal is a prompt signal.

* * * * *